(12) United States Patent
Sokoloff

(10) Patent No.: US 7,993,278 B2
(45) Date of Patent: Aug. 9, 2011

(54) METHOD AND SYSTEM FOR NON-INVASIVELY MEASURING PULMONARY FUNCTION

(76) Inventor: Michael Sokoloff, Cincinnati, OH (US)

( * ) Notice: Subject to any disclaimer, the term of this patent is extended or adjusted under 35 U.S.C. 154(b) by 1426 days.

(21) Appl. No.: 11/485,394

(22) Filed: Jul. 13, 2006

(65) Prior Publication Data

US 2007/0021681 A1    Jan. 25, 2007

Related U.S. Application Data

(60) Provisional application No. 60/699,183, filed on Jul. 14, 2005.

(51) Int. Cl.
*A61B 5/08* (2006.01)
(52) U.S. Cl. .................................................. 600/529
(58) Field of Classification Search ........... 600/529–543
See application file for complete search history.

(56) References Cited

U.S. PATENT DOCUMENTS

| | | | |
|---|---|---|---|
| 3,785,370 A | 1/1974 | Richards et al. | |
| 4,221,224 A | 9/1980 | Clark | |
| 4,307,730 A * | 12/1981 | Korn | 600/541 |
| 5,069,220 A | 12/1991 | Casparie et al. | |
| 5,119,825 A * | 6/1992 | Huhn | 600/529 |
| 5,540,233 A * | 7/1996 | Larsson et al. | 600/538 |
| 5,957,128 A | 9/1999 | Hecker et al. | |
| 6,139,506 A | 10/2000 | Heinonen | |
| 6,287,264 B1 | 9/2001 | Hoffman | |
| 6,306,099 B1 | 10/2001 | Morris | |
| 6,544,191 B2 | 4/2003 | Koch et al. | |
| 6,723,055 B2 | 4/2004 | Hoffman | |
| 6,983,750 B2 | 1/2006 | Heinonen | |
| 7,662,107 B2 * | 2/2010 | Dicks et al. | 600/532 |
| 2002/0052560 A1 * | 5/2002 | Koch et al. | 600/538 |
| 2003/0023180 A1 * | 1/2003 | Mault | 600/531 |
| 2003/0100843 A1 | 5/2003 | Hoffman | |
| 2004/0230113 A1 * | 11/2004 | Bolam et al. | 600/410 |
| 2006/0264772 A1 * | 11/2006 | Aljuri et al. | 600/538 |
| 2009/0137919 A1 * | 5/2009 | Bar-Lavie et al. | 600/538 |

OTHER PUBLICATIONS

Wagers, Scott, M.D.; "Polarized helium: Changing our view of asthma"; J Allergy Clin Immunol 2003; 111:1201-2; pp. 1201-1202; Burlington, Vermont.

(Continued)

*Primary Examiner* — Charles A Marmor, II
*Assistant Examiner* — Karen Toth
(74) *Attorney, Agent, or Firm* — Eric W. Guttag; Eric W. Guttag IP Law Office

(57) ABSTRACT

A method and system for measuring pulmonary function. The method comprises the following steps of: (1) providing or obtaining a measurement of a subject breathing an inert gas composition; (2) providing or obtaining a measurement of the subject breathing a replacement gas composition; and (3) extracting parameters from these two measurements. The system comprises: (a) a gas supply; (b) a subject interface; (c) an inert gas concentration measuring device, wherein the system; and (d) means for extracting parameters from the measurements by the inert gas concentration measuring device: (1) obtains a measurement with the measuring device through the subject interface of a subject breathing an inert gas composition supplied from the gas supply; (2) obtains a measurement with the measuring device through the subject interface of the subject breathing a replacement gas composition supplied from the gas supply; and (3) extracts parameters with the parameter extracting means from these two measurements.

24 Claims, 8 Drawing Sheets

OTHER PUBLICATIONS

U.S. Department of Health and Human Services, Public Health Service, NIH, "Practical Guide for the Diagnosis and Management of Asthma"; National Asthma Education and Prevention; NIH Publication 97-4053; Oct. 1997; pp. 1-5; United States of America.

Spahn, Joseph D., et al., "Is Forced Expiratory Volume in One Second the Best Measure of Severity in Childhood Asthma"; Am J Respir Crit Care Med; vol. 169, pp. 784-786, 2004; Denver.

Levitzky, Michael G., Ph.D.; "Ventilation-Perfusion Relationships"; Pulmonary Physiology; Sixth Edition; pp. 118-119; New Orleans, Louisiana, 2000.

West, John B., M.D., Ph.D., D.Sc.; "Chapter 2: Ventilation: How Gas Gets to the Alveoli"; Respiratory Physiology The Essentials; Sixth Edition; pp. 11-15; LaJolla, California, 2003.

Lyons, Louis; "Chapter 6: Monte Carlo calculations"; Statistics for Nuclear and Particle Physicists; Cambridge University Press; pp. 161-187; Victoria, Australia, 1986.

* cited by examiner

METHOD AND SYSTEM FOR NON-INVASIVELY MEASURING PULMONARY FUNCTION

CROSS-REFERENCE TO RELATED APPLICATIONS

This application makes reference to and claims the benefit of the following U.S. Provisional Patent Application No. 60/699,183, filed Jul. 14, 2005. The entire disclosure and contents of the foregoing Provisional Application is hereby incorporated by reference.

BACKGROUND

1. Field of the Invention

This invention generally relates to a method and system for non-invasively measuring pulmonary function, and more particularly to a method and system that provides quantitative descriptions of lung volumes which are exchanging air more slowly than the bulk of the lung volume.

2. Related Art

The importance of characterizing the complexity of pulmonary function in diagnosing asthma and in assessing potential treatments for asthma has been reviewed recently in the literature. See, e.g., S. Wagers, "Polarized Helium: Changing Our View of Asthma," *J. Allergy Clin. Immun.* 1201 (June 2003). Characterizing the complexity of pulmonary function is also useful in diagnosing and in assessing potential treatments for Chronic Obstructive Pulmonary Disease (COPD), as well as many other pulmonary conditions which are familiar to medical experts.

The most common clinical test for asthma is the Forced Expiratory Volume in One Second (FEV1) test. The FEV1 test is often used in conjunction with the Forced Vital Capacity (FVC) test. For example, NIH guidelines specify that a FEV1 value <80% of the predicted value, or a FEV1/FVC value <65% of the predicted value, is an appropriate method for diagnosing asthma. See NIH publication no. 97-4053, *Practical Guide for the Diagnosis and Management of Asthma*, (1997). The precision of such measurements is about 10%. While a real correlation between the diagnostic thresholds and clinical expression of symptoms exists, most children with asthma have FEV1 values above the NIH threshold value. See J. Spahn, et al., "Is Forced Expiratory Volume in One Second the Best Measure of Severity in Childhood Asthma?," *Am. J. Respir. Crit. Care Med.* 169:784 (2004). The FEV1 and FVC tests are also used to diagnose COPD and other pulmonary disorders.

While clinical tests exist for identifying patients suffering from asthma, COPD, and related pathologies, medical practitioners and investigators have identified the need for better tests to more correctly identify the nature and level of small airway constriction or blockage both in diagnosing these pathologies and in assessing the benefits of the treatments of these pathologies. Medical practitioners and investigators have also identified the need for better measures to quantify pulmonary pathologies.

SUMMARY

According to a first broad aspect of the present invention, there is provided a method for identifying and quantifying the presence of partially blocked or constricted small airways in the lung of a subject related to a respiratory pathology with greater precision. The method comprises the following steps of: (1) providing or obtaining a measurement of a subject breathing an inert gas composition; (2) providing or obtaining a measurement of the subject breathing a replacement gas composition; and (3) extracting parameters from the inert gas composition measurement and the replacement gas composition measurement that define an inert gas concentration function, $f(t)$, to thereby identify and quantify any presence of a partially blocked or constricted small airway in the lung of the subject, wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time. A measure of impaired pulmonary function, the overall impairment, I, may also be determined using these parameters, as described below, as well as the time for one breath, $t_b$, as described below, and the fraction of the lung's volume exchanged in one breath, $F_{breath}$, as described below.

According to a second broad aspect of the present invention, there is also provided a system for extracting these parameters to define the extent and the level of small airway restriction in the lung of a subject, as well as provide a new measure of pulmonary impairment, the overall impairment, I, from measurements of the non-exponential decay of inhaled inert gas concentrations in exhaled breath as a function of time. The system comprises: (a) a gas supply; (b) a subject interface; (c) an inert gas concentration measuring device; and (d) means for extracting parameters from measurements by the inert gas concentration measuring device, wherein the system: (1) obtains a measurement with the inert gas concentration measuring device through the subject interface of a subject breathing an inert gas composition supplied from the gas supply; (2) obtains a measurement with the inert gas concentration measuring device through the subject interface of the subject breathing a replacement gas composition supplied from the gas supply; and (3) extracts parameters with the parameter extracting means from the inert gas composition measurement and the replacement gas composition measurement that define an inert gas concentration function, $f(t)$, to thereby define the extent and the level of small airway restriction in the lung of the subject, wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time. A measure of impaired pulmonary function, the overall impairment, I, as described below, may be determined using these parameters, as well as the time for one breath, $t_b$, as described below, and the fraction of the lung's volume exchanged in one breath, $F_{breath}$, as described below.

According to a third broad aspect of the present invention, there is further provided a method for quantifying inert gas washout from the circulatory system. The method comprises the steps of: (1) providing or obtaining a measurement of a subject breathing an inert gas composition; (2) providing or obtaining a measurement of the subject breathing a replacement gas composition; and (3) extracting parameters from the inert gas composition measurement and the replacement gas composition measurement that define an inert gas concentration function, $f(t)$, to thereby quantify the inert gas washout from the circulatory system of the subject, wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time. A measure of the inert gas exchange rate between the lung and the circulatory system, analogous to the overall pulmonary impairment I, may also be determined using these parameters, as described below, as well as the time for one breath, $t_b$, as described below.

According to a fourth broad aspect of the present invention, there is also provided a system for quantifying inert gas washout from the circulatory system of a subject. The system comprises: (a) a gas supply; (b) a subject interface; (c) an inert gas concentration measuring device; and means for extracting parameters from measurements by the inert gas concentration measuring device, wherein the system: (1) obtains a measurement with the inert gas concentration measuring device through the subject interface of a subject breathing an inert gas composition supplied from the gas supply; (2) obtains a measurement with the inert gas concentration measuring device through the subject interface of the subject breathing a replacement gas composition supplied from the gas supply; and (3) extracts parameters with the parameter extracting means from the inert gas composition measurement and the replacement gas composition measurement that define an inert gas concentration function, $f(t)$, wherein the circulatory system of the subject is treated as an extension of the lung of the subject to thereby quantify the inert gas washout from the circulatory system of the subject, and wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time. A measure of inert gas exchange between the lung and the circulatory system, analogous to the overall pulmonary impairment I, may also be determined using these parameters, as described below, as well as the time for one breath, $t_b$, as described below.

BRIEF DESCRIPTION OF THE DRAWINGS

The invention will be described in conjunction with the accompanying drawings, in which.

DETAILED DESCRIPTION

Figure 1:
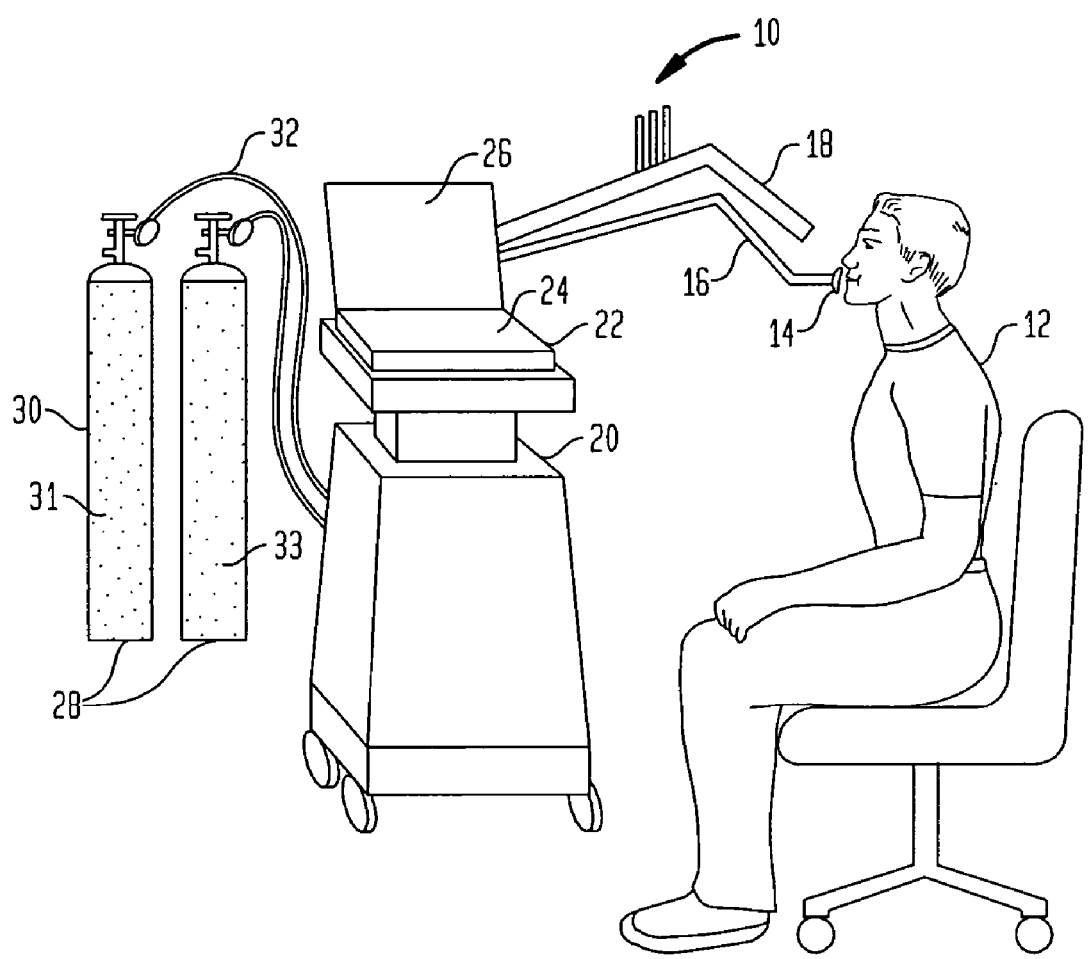
FIG. 1 is a perspective view of an embodiment of the system of the present invention with a seated subject whose pulmonary function is to be measured.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "inert gas composition" refers to any physiologically acceptable composition comprising one or more (e.g., mixtures of two or more) physiologically acceptable gases which may be safely breathed for the duration of the measurements and which contain at least one physiologically acceptable inert gas. Suitable physiologically acceptable inert gases for use herein include nitrogen, helium, neon, argon, krypton, xenon, radon, sulfur hexafluoride, a gaseous perfluorocarbon, etc., as well as mixtures of these gases. The inert gas composition may also and often comprises non-inert gases, for example, oxygen.

For the purposes of the present invention, the term "replacement gas composition" refers to any physiologically acceptable composition comprising one or more (e.g., mixtures of two or more) physiologically acceptable gases which may be safely breathed for the duration of a measurement and which lacks (i.e., does not contain) at least one of the physiologically acceptable inert gases present in the corresponding inert gas composition. For example, the replacement gas composition may comprise solely a non-inert gas such as oxygen, may comprise a mixture of inert gas(es) and non-inert gas(es), etc.

For the purposes of the present invention, the term "measurement of a subject breathing an inert gas composition" refers to one or more measurements of at least one inert gas concentration in a subject's exhaled breath taken while the subject is breathing an inert gas composition, and including the time(s) at which the measurement(s) is (are) made.

For the purposes of the present invention, the term "measurement of a subject breathing a replacement gas composition" refers to one or more measurements of at least one inert gas concentration in a subject's exhaled breath taken while the subject is breathing a replacement gas composition, and including the time(s) at which the measurement(s) is (are) made.

For the purposes of the present invention, the term "breathing" may refer to a subject inhaling, exhaling or both inhaling and exhaling.

For the purposes of the present invention, the term "subject" refers to the individual whose breath is being measured, obtained, determined analyzed, etc., by an embodiment of a method and/or system of the present invention.

For the purposes of the present invention, the term "inert gas concentration function" refers to a function of time, $f(t)$, whose values at times $t_i$ are defined by measurements of a subject breathing a replacement gas composition from which, for example, parameters may be extracted to define different effective volumes of the lung of the subject, as illustrated by equation (1) below.

For the purposes of the present invention, the term "exponential term" refers to mathematical expression of the form $Ce^{-\Gamma t}$ where C and $\Gamma$ have values which do not vary with the independent variable, indicated here by the symbol t.

For the purpose of the present invention, the term "exponential terms defining different effective volumes of the lung of the subject" refers to the exponential terms in a mathematical equation which, in a simple model, correspond to portions of the lung of the subject, each of which may have a characteristic gas decay (or exchange) rate, $\Gamma_i$, and a corresponding coefficient, $f_i$, which does not vary with time (where "i" represents one of the possible exponential terms), and which may be described equivalently as having a different characteristic inert gas concentration decay rate as observed by using a multi-breath washout (MBW) technique or measurement.

For the purposes of the present invention, the term "the sum of at least two exponential terms" means that the inert gas concentration function, $f(t)$, includes at least two exponential terms with characteristic decay rates $\Gamma_1$ and $\Gamma_2$ and corresponding coefficient $f_1$ and $f_2$, but which may include more than two exponentials terms with characteristic decay rates $\Gamma_3$, $\Gamma_4$, etc., and corresponding coefficients $f_3$, $f_4$, etc.

For the purposes of the present invention, the term "characteristic inert gas concentration decay rate" (also referred to as the "exchange rate") refers to the mathematical parameter $\Gamma$ (e.g., $\Gamma_1$, $\Gamma_2$, etc.) which describes the decay rate per unit time in an exponential decay according to the following equation (a):

$$f(t)=f(0)e^{-\Gamma t} \quad (a)$$

where t is the time, and $f(0)$ is the value of function $f(t)$ at t=0. A decay rate which follows equation (a) when $\Gamma$ is constant is said to be an "exponential decay." Conversely, a decay rate which does not follow equation (a) when $\Gamma$ is constant is said to be a "non-exponential decay."

For the purposes of the present invention, the term "decay time" (also referred to as the "exchange time") is characterized by the symbol, $\tau$, for example, $\tau_1$, $\tau_2$, etc., and is also the inverse of the exchange rate, $\Gamma$, for example, $\Gamma_1$, $\Gamma_2$, etc.

For the purposes of the present invention, the term "tidal flow rate" refers to the rate at which a subject inhales and exhales gases from the lung, as is commonly understood in the medical community. The tidal flow rate may be quantified in terms of the tidal volume per inhalation or exhalation where the tidal volume refers to the quantity of gas inhaled during inhalation, or expelled during exhalation, by the subject. See, e.g., West, *Respiratory Physiology, The Essentials* (Lippincott Williams & Wilkins 2000).

For the purposes of the present invention, the term "initial exponential decay rate" refers to $\Gamma_1$, while the "later exponential decay rate(s)" refers to $\Gamma_2$, etc. $\Gamma_1$ may also be referred to as the "initial exchange rate" and is the inverse of $\tau_1$, while $\Gamma_2$, etc., may also be referred to as the "later exchange rate(s)" and is (are) the inverse of $\tau_2$, etc.

For the purposes of the present invention, the term "respiratory pathology" refers to a disease state, medical disorder, etc., which reduces, lessens, restricts, etc., the pulmonary function of a subject, as would be commonly understood by the medical community, including, for example, asthma, Chronic Obstructive Pulmonary Disease (COPD), cystic fibrosis, etc.

For the purposes of the present invention, the term "partially blocked or constricted small airways in the lung" refers to a pathological condition which restricts the flow of air and other respired gases through the small airways in the lung of the subject, e.g., due to mechanical blockage produced by the presence, for example, of mucus or other fluids, narrowing by fibrosis, swelling of tissue resulting from inflammation, constriction resulting from muscular contraction, etc. The pathological condition which restricts the flow through the small airways may be naturally occurring, or may be medically or pharmacologically induced.

For the purposes of the present invention, the term "anatomic dead space" refers to, as commonly understood in the medical community, the volume of the conducting airways of the respiratory system. See, e.g., West, *Respiratory Physiology, The Essentials* (Lippincott Williams & Wilkins 2000).

For the purposes of the present invention, the term "small airways" refers to those airways of the lung commonly understood in the medical community as small airways.

For the purposes of the present invention, the term "parameter" refers to a quantity in a mathematical expression for a function and having a symbol which is intended to denote a value which does not vary with respect to the independent variable. For example, as illustrated in equation (1) below, the independent variable is $t_i$, while the parameters are $f_1$, $f_2$, $\tau_1$ and $\tau_2$.

For the purposes of the present invention, the term "extracting parameters" refers to a mathematical procedure for obtaining, acquiring, determining, calculating, etc., one or more parameters from measurements and which are used to define a function of an independent variables to provide, for example, the best agreement between predicted values of the function and the observed values. For example, in equation (2) below, the independent variable is $t_i$, the parameters are $f_1$, $f_2$, $\tau_1$ and $\tau_2$, and the best agreement between the predicted and the observed values occurs when the variable $\chi^2$ is minimized For the purposes of the present invention, the terms "Monte Carlo method," "Monte Carlo experiment," and "Monte Carlo simulation" refer interchangeably to a computational method for simulating the behavior of various physical and mathematical systems using random numbers, as commonly understood in the fields of, for example, experimental particle physics, other fields of physics and engineering, etc. See, e.g., Lyons, *Statistics and Nuclear Physics* (Cambridge University Press 1986).

For the purposes of the present invention, the term "ensembles of experiments" refers to repetitions of Monte Carlo simulations of measurements in which the parameters defining the mathematical equation describing a subject's pulmonary function take on fixed values, but where random numbers used to generate the outcomes vary.

For the purposes of the present invention, the term "fractional error" refers to the ratio of the uncertainty in a measured quantity with respect to the measured value of the quantity itself. For example, the fractional error in the quantity C may be calculated as $\Delta C/C$, where $\Delta C$ is the uncertainty in C. In a mathematical simulation of a real measurement, fractional error refers to the corresponding ratio where $\Delta C$ is the simulated uncertainty in C and C is the simulated value.

For the purposes of the present invention, the term "normal pulmonary function" refers to a pulmonary function which would be commonly understood by the medical community as being healthy, i.e., a pulmonary function which is normal, standard, average, etc., for an individual.

For the purposes of the present invention, the term "impaired pulmonary function" refers to a pulmonary function which would be commonly understood by the medical community as being unhealthy, i.e., a pulmonary function which is below or less than normal, standard, average, etc., for an individual. Subjects having impaired pulmonary function would include those afflicted by or suffering from asthma, Chronic Obstructive Pulmonary Disease (COPD), cystic fibrosis, etc., i.e., a naturally occurring impairment, as well as those subjects having impaired pulmonary function that is induced medically or pharmacologically, e.g., through the use of drugs.

For the purposes of the present invention, the term "overall impairment" (hereafter characterized as "I") refers to a mathematically defined expression of the impairment of pulmonary function of the lung of a subject as whole, and as illustrated in equation (6) below.

For the purposes of the present invention, the terms "one breath" or "single breath" refer interchangeably to one inspiration of a gas composition into the lungs by a subject, followed by one exhalation from the lungs of the subject.

For the purposes of the present invention, the terms "time for one breath" or "time for a single breath" ($t_b$) refer interchangeably to the time period defined by one inspiration of a gas composition into the lungs by a subject, to the next inspiration of a gas composition into the lungs of the subject.

For the purposes of the present invention, the term "circulatory system" refers to those portions of the individual which normally transport and/or contain blood, as commonly understood in the medical community, including, but not limited to arteries, veins, capillaries, the heart, the lungs, etc.

For the purposes of the present invention, the term "lung" may refer to one lung of the subject, or both lungs of the subject.

For the purposes of the present invention, the term "<x>", for example, <$f$>, refers to the average, calculated as the arithmetic mean, of the indicated value, (e.g., $f$).

For the purposes of the present invention, the term "add in quadrature" refers to a mathematical calculation performed using the following steps: squaring each of two or more values; adding (summing) these squared values together; and taking the square root of these summed values. For example, adding in quadrature the values represented by the symbols x and y may be represented by the equation $\sqrt{x^2+y^2}$.

For the purposes of the present invention, the term "effective dynamic range" refers to an inert gas concentration measurement dynamic range, relative to an initial inert gas concentration level. For example, if the initial inert gas concentration level is 0.80 and the minimum inert gas concentration level that can be measured is $0.80 \times 10^{-4}$, the effective dynamic range will be four orders of magnitude, i.e., a factor of 10000; if the initial inert gas concentration level is 0.08 and the minimum inert gas concentration level that can be measured is $0.80 \times 10^{-4}$, the effective dynamic range will be three orders of magnitude, i.e., a factor of 1000.

Description

The present invention relates to embodiments of a method and system which obtain and/or provide measurements of exhaled inert gas and replacement gas compositions by a subject and to extract from those measurements parameters that: (1) identify and quantify any presence of a partially blocked or constricted small airway in the lung of the subject; (2) define the extent and the level of small airway restriction in the lung of the subject; and/or (3) quantify the inert gas washout from the circulatory system of the subject The benefits of various embodiments of the method and system of the present invention may be realized by using an extension of an inert gas multi-breath washout (MBW) technique. For example, a subject breathes an inert gas composition including one or more physiologically acceptable inert gases until saturation of the inert gas concentration(s) in the lung is (are) achieved at a predetermined level(s), and then breathes a replacement gas composition (which lacks at least one of the inert gases present in the corresponding inert gas composition) for the duration of the measurement. The subject's exhaled breath is monitored, and the concentration of the inert gas in the exhaled breath is measured as a function of time, $f(t)$. This function $f(t)$ may be analyzed mathematically and the parameters extracted therefrom compared to those similarly measured for individuals with normal pulmonary function and to those for individuals with impaired pulmonary function (e.g., those with asthma, COPD, etc.). The differences between normal and impaired pulmonary function depend upon, as well as reflect, the portion(s) of the lung which is (are) partially constricted or blocked, the level of restriction in that (those) portion(s) of the lung, etc.

In a simple model of the lung, the inert gas concentration measured in a healthy subject breathing a replacement gas composition decays exponentially with time. To the extent that there are partially blocked or constricted airways, a non-exponential curve or tail may be observed after many volume exchanges. Inert gas MBW measurements are commonly made using, for example, atmospheric nitrogen as the inert gas. The measured exponential decay rate of the nitrogen fraction is also commonly measured over about two orders of magnitude and may be combined with a measured tidal flow rate to determine the subject's lung volume. Measuring inert gas concentrations over two orders of magnitude allows measurement of non-exponential distributions only when agonists such as histamine, methacholine, cold air, etc., provoke profound reactions. By instead extending the dynamic range of the measurements to at least three or four orders of magnitude, as well as extracting parameters describing both the initial exponential decay rate ($\Gamma_1$) of the inert gas concentration, as well as the later exponential decay rate (e.g., $\Gamma_2$), various embodiments of the method and system of the present invention may provide measurements related to both the extent and level of naturally occurring, but pathological, partial constriction or blockage of small airways in the lung of a subject.

1. Dynamic Pulmonary Function Measuring System

Figure 2:
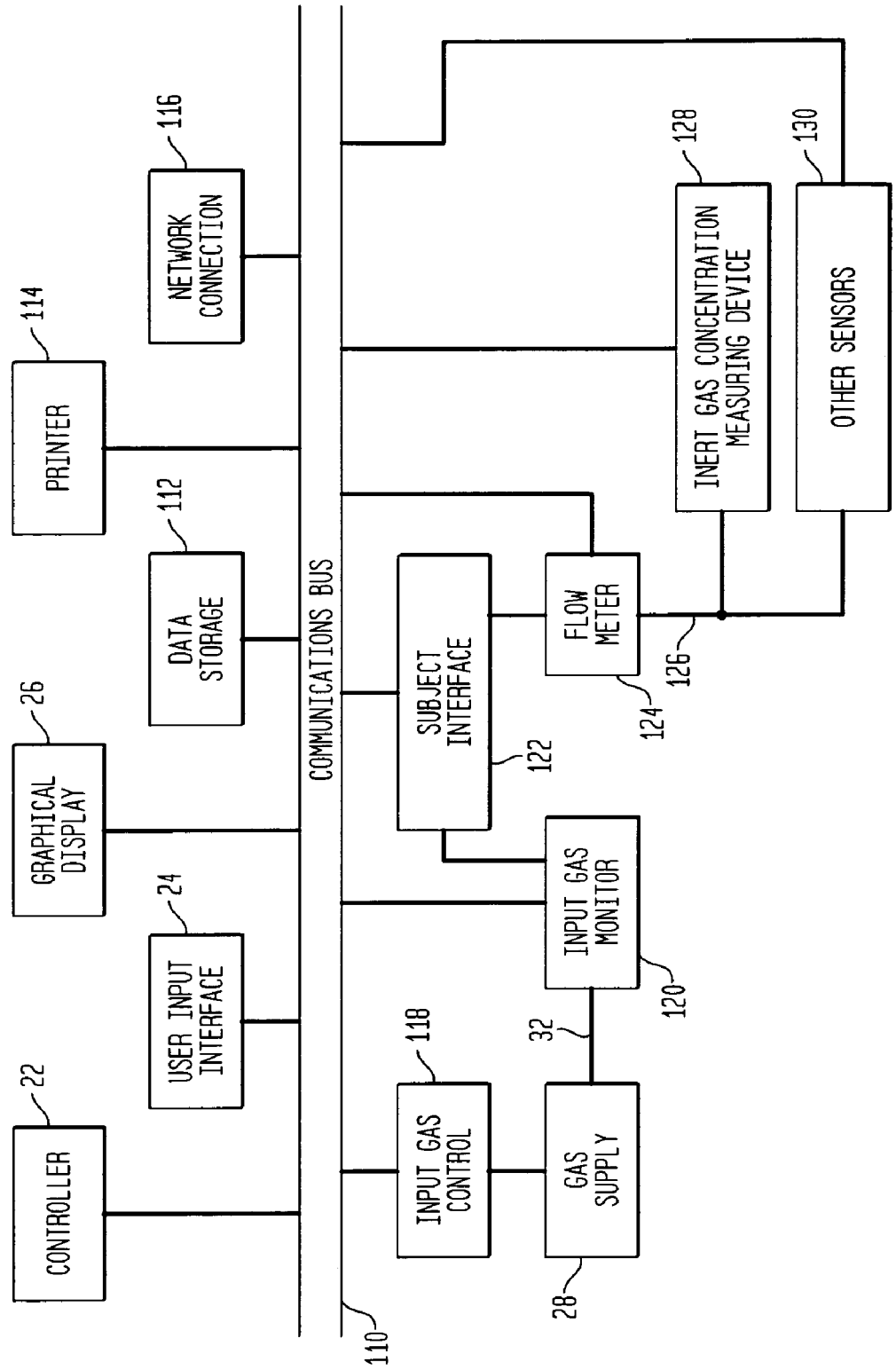
FIG. 2 is a block diagram illustrating the system of FIG. 1 and showing various components thereof.
Figure 3:
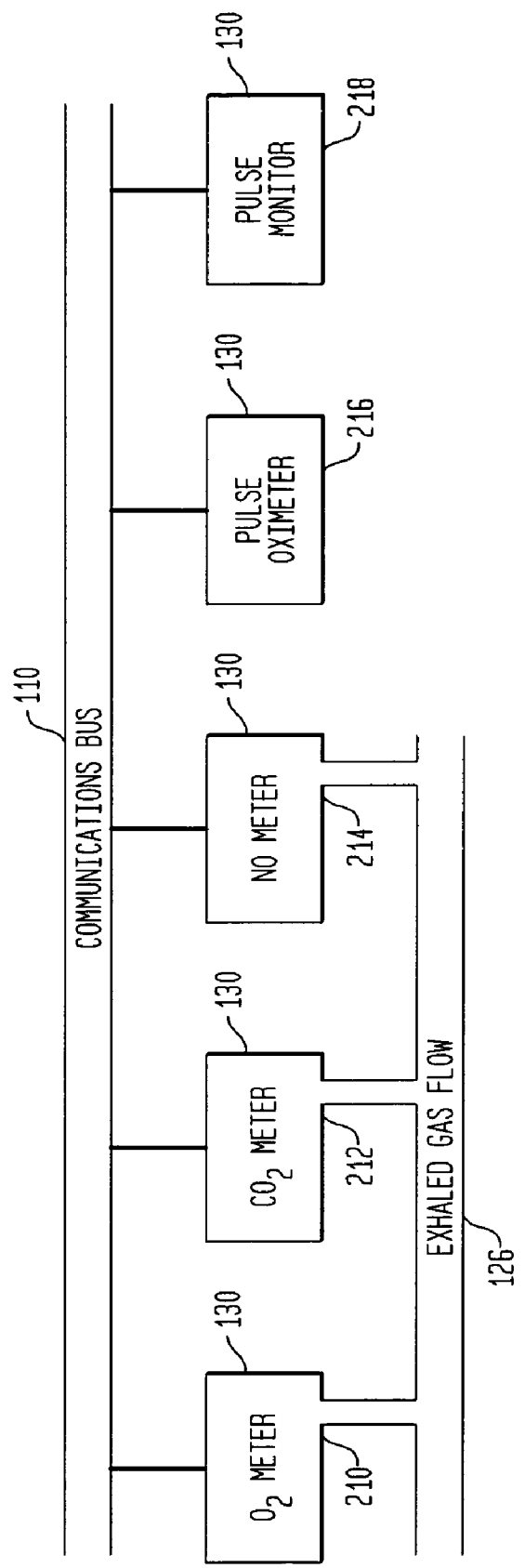
FIG. 3 is a block diagram illustrating possible auxiliary sensors which may be used in conjunction with the inert gas concentration measuring device shown in FIG. 2.

Referring to FIGS. 1-4, there is shown an embodiment of a dynamic pulmonary function measuring system 10 of the present invention. As shown in FIGS. 1 and 2, system 10 includes a gas supply 28, a subject interface 122, an inert gas concentration measuring device 128, and a controller 22.

In the operation of system 10, a subject 12 breathes in (inhales) and out (exhales) of a mouthpiece 14 connected to, for example, rigid tubing 16 whose position may be adjusted using, for example, a pivoting arm 18. In one embodiment, gas supply 28 may comprise pressurized cylinders 30 of pre-mixed gas(es) 31 and 33 connected to the rest of system 10 by using tubing 32 which does not leak. As shown in FIG. 1, the externally visible elements of the system 10 may comprise controller 22 (for example, as part of a personal computer or workstation) with an operator input interface (for example, a computer keyboard) 24, and a graphical display (for example, a computer monitor) 26. The remaining components of system 10 (which are not visible) may be contained within enclosure 20.

FIG. 2 illustrates and shows the electronic logic components which system 10 may comprise. As shown in FIG. 2, system 10 may comprise controller 22, operator input interface 24, graphical display 26, data storage 112, printer 114, and network connection 116, all of which may be connected to a communications bus 110. The input gas control 118 may also be connected to communications bus 110 and gas supply 28. Gases 31 and 33 flow through tubing 32 to the input gas monitor 120 which may also be connected to communications bus 110. Gas flows from input gas monitor 120 to subject interface system 122 which may have sensors and valves (not shown) to control the flow of gas to and from subject 12. Gas exhaled from the lungs of subject 12 flows into subject interface system 122, and then from subject interface system 122 through a flow meter 124 and into inert gas concentration measuring device 128, and optionally, in parallel, to a variety of other, auxiliary sensors 130 shown in FIG. 3. Some of the auxiliary sensors 130 sample the exhaled gas (for example, an $O_2$ meter 210, a $CO_2$ meter 212, and a nitric oxide (NO) meter 214 shown in FIG. 3), and some do not (for example, a pulse oximeter 216 and a simple pulse monitor 218 shown in FIG. 3).

Figure 4:
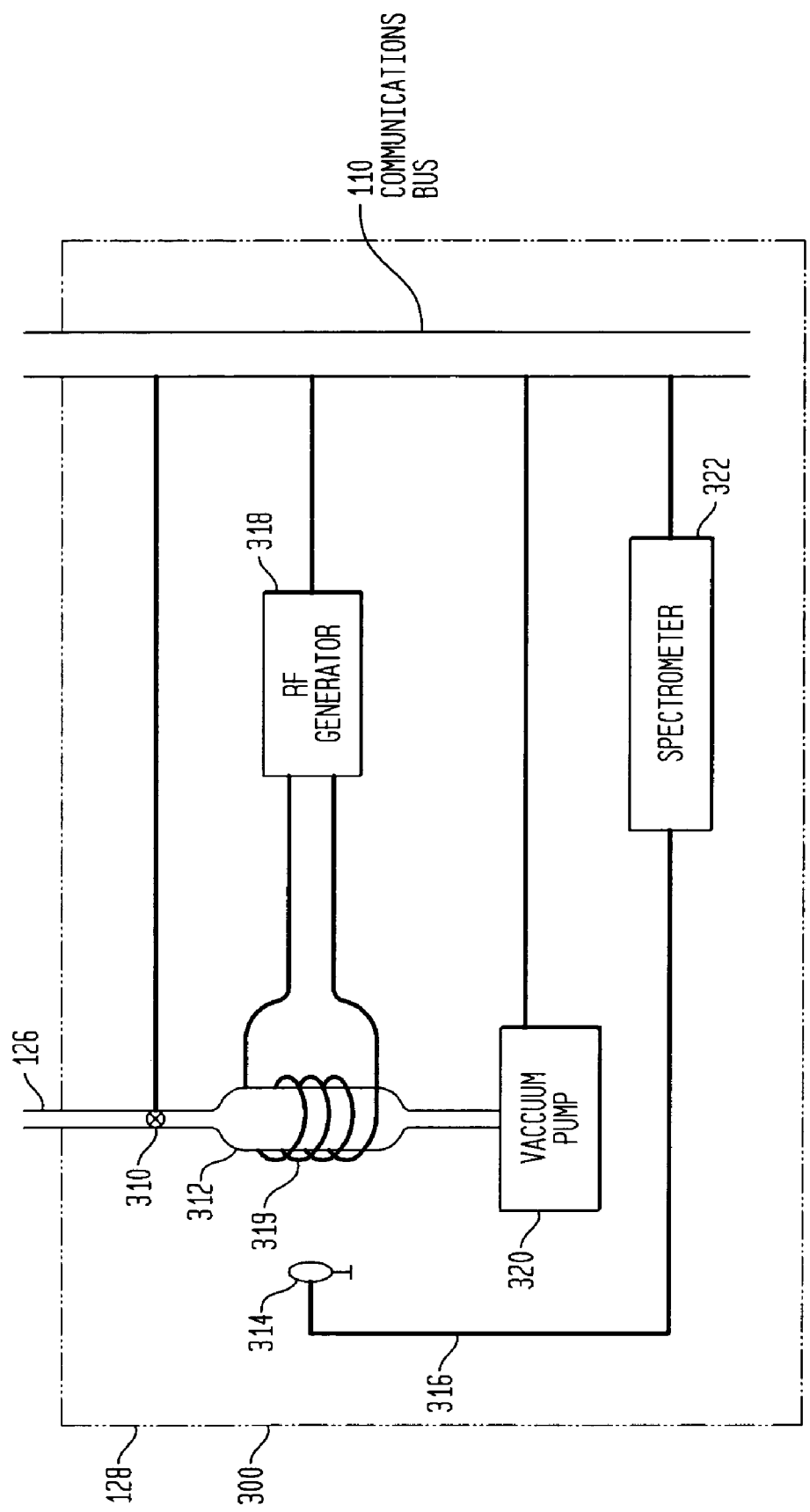
FIG. 4 shows an atomic emissions spectrometer system which may be used as the inert gas concentration measuring device of FIG. 2.

Inert gas concentration measuring device 128 of FIG. 2 may be any device which is capable of measuring inert gas concentrations with the requisite degree of precision needed or desired. Examples of devices 128 include, but are not limited to, commercially available atmospheric sampling systems based on mass spectroscopy (such as the SRS QMS200 high pressure gas analyzer), the atomic emissions (AE) spectroscopy system 300 shown in FIG. 4, etc. Referring to FIGS. 2 and 4, system 300 samples the exhaled gas which enters through tube 126 (see FIG. 2) and passes through a pin-hole valve 310. The exhaled gas may be maintained at a fixed pressure in the range, for example, of from about 20 to about 100 millitorr in a glass vessel 312 by using vacuum pump 320. A radio frequency (RF) generator 318 produces an RF signal in a conducting coil 319 which encloses the glass vessel 312 and which, in turn, creates a plasma from the enclosed gas. Light emitted by the plasma is focused by lens 314 onto an optical fiber 316 which transmits the focused light to a spectrometer 322 which measures the intensity of the spectral lines (optical, infrared, and/or ultraviolet) associated with the inert gas(es) of interest and any other gases of interest.

2. Method for Making Measurements of Subject with System

Figure 5:
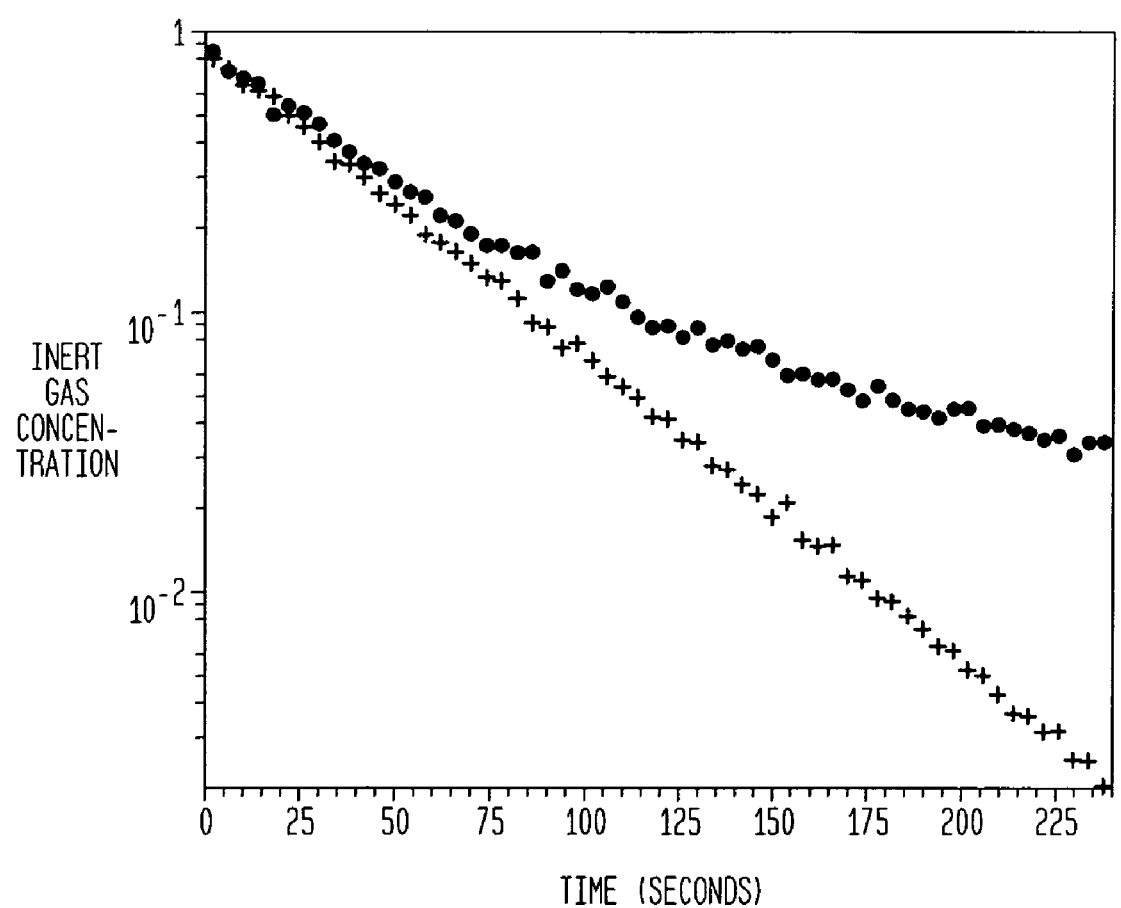
FIG. 5 is a graphical representation of a computer simulation of a nitrogen washout measurement with parameters corresponding to those extracted from the measurement shown in Levitzky, *Pulmonary Physiology* (McGraw-Hill, New York, 2003), p. 119, for a normal subject before (indicated by crosses or plus signs) and after (indicated by circles) inhalation of a histamine aerosol.

In an embodiment of obtaining measurements from subject 12 by using system 10, an operator (not shown) makes sure that system 10 has been turned on properly, that gas supply 28 is functioning correctly, and that the inert gas concentration measuring device 128 is properly calibrated. Assuming the inert gas does not comprise nitrogen, subject 12 breathes, at a natural and relaxed rate, a gas composition 31 that contains the inert gas(es) with the desired initial inert gas concentration until saturation at that level is achieved throughout the lung, typically within, for example, approximately five minutes. During this period, the inert gas concentration in the exhaled gas may be monitored by inert gas concentration measuring device 128 to determine when saturation of the lungs of subject 12 has been achieved. This monitoring may be done using signals generated in inert gas concentration measuring device 128 and transmitted to controller 22 which may have software and/or firmware for interpreting these signals and converting them into inert gas concentrations. Once suitable saturation has been achieved, subject 12 begins to breathe the replacement gas composition 33, again at a relaxed and natural rate. (If the inert gas instead comprises nitrogen, the initial nitrogen level is monitored before the subject 12 begins to breathe the replacement gas composition 33.) In the period during which subject 12 breathes the replacement gas composition 33, the inert gas concentration in the exhaled breath may be monitored until either the concentration falls below a target level (e.g., a factor of from about 1000 to about 10000 below the initial saturation level, as indicated, for example, by the horizontal dashed line in FIG. 8), or earlier if the operator or software (and/or firmware) in controller 22 determines that the non-exponential character of the function $f(t)$ may be determined with sufficient precision, as would be the case where the measurements look like, for example, the data points shown as circles in FIG. 5. All signals from inert gas concentration measuring device 128 generated while subject 12 is breathing inert gas composition 31 and the replacement gas composition 33, as well as the times at which these measurements are made, may be recorded by data storage device 112.

3. Method for Extracting Parameters from Measurements

In an embodiment of extracting parameters from the measurements obtained from subject 12 by using system 10, the recorded data may be analyzed (i.e., parameters extracted), either by using controller 22 and/or by using, for example, another computer processor (not shown), in, for example, various stages. For example, the first stage of the analysis may extract from the raw signals the actual inert gas concentrations at specific times. The second stage of the analysis may extract, from all of the measurements made in each breath, one or more measurements to be used in determining the shape of function $f(t)$. During a single exhalation by subject 12, the exhaled inert gas concentration may vary significantly as a function of time. In the first phase of exhalation, the exhaled gas is expelled from the anatomic dead space and not from the small airways. In the later phases of exhalation, the exhaled gas comprises a mixture of gases expelled from the anatomic dead space and from the small airways, and eventually later primarily from the small airways. The analysis which is carried out may use: (a) an inert gas concentration averaged over each breath; (b) an average inert gas concentration over the phase which measures gas expelled (primarily) from the small airways; (c) the lowest inert gas concentration measured during each breath; and/or (d) all measurements which measure gas expelled (primarily) from the small airways. To the extent that the duration of each breath is different, or to the extent that the flow rate is not uniform, an effective time may be computed for each measurement. The third stage of the analysis may fit the extracted data (e.g., the average inert gas concentration measured in each breath during the respective phase when the gas expelled from the small airways is measured and the corresponding time) to a sum of, for example, two characteristic decay times $\tau_1$ and $\tau_2$ and two corresponding mathematical fractions $f_1$ and $f_2$ using a $\chi^2$ minimization algorithm. The predicted value of $f(t)$ in the $i^{th}$ breath, $f(t_i)^{pred}$, may be written as the following equation (1):

$$f(t_i)^{pred} = f_1 e^{-t_i/\tau_1} + f_2 e^{-t_i/\tau_2} \qquad (1)$$

where $t_i$ is the corresponding time at which the $i^{th}$ measurement is taken. The fitted values of the parameters $f_1, f_2, \tau_1,$ and $\tau_2$ may be determined by minimizing $\chi^2$ which is defined according to the following equation (2):

$$\chi^2 = \sum_i \frac{(f(t_i)^{pred} - f(t_i))^2}{\sigma_i^2} \qquad (2)$$

with respect to the parameters $f_1, f_2, \tau_1,$ and $\tau_2$. The variances $\sigma_i^2$ in the denominator are the expected uncertainties (statistical and systematic) associated with $i^{th}$ measured point. From these parameters and the typical duration of a single breath, $t_b$, the overall impairment I (as defined below) may be calculated. (Sums involving more than two characteristic decay times $\tau_1$ and $\tau_2$ and more than two corresponding mathematical fractions $f_1$ and $f_2$ may be similarly carried out.)

The benefits of the method and system of the present invention may be realized when the parameters extracted from the measurements are used to characterize pulmonary impairment quantitatively. Specifically, the extracted parameters may be understood by considering a simple model of gas exchange between the lung and the outside world during respiration. For comparison, NIH guidelines specify that an FEV1 value <80% of the predicted value, or an FEV1/FVC value <65% of the predicted value, may be used as an appropriate method for diagnosing asthma. See NIH publication no. 97-4053, *Practical Guide for the Diagnosis and Management of Asthma*, (1997). These values indicate impairments of roughly 20%. Inducing an allergic reaction using a histamine or methacholine agonist may lead to almost full blockage of 12% of the small airways. This is shown graphically in FIG. 5 which depicts the results of a simulation of nitrogen washout with parameters corresponding to those extracted from the measurement shown in Levitzky, M. G., *Pulmonary Physiology* (McGraw-Hill, New York, 2003), p. 119, and corresponds to an overall impairment of 10%, as overall impairment (I) is defined below.

In a normal subject 12, 100% of the small airways participate in respiration with a characteristic exchange time $\tau$. In the presence of partial blockage one may assume, for example, that there are two components (i.e., mathematical fractions) of respiration, $f_1$ and $f_2$, with corresponding characteristic exchange times (i.e., decay times) $\tau_1$ and $\tau_2$. These characteristic exchange times/decay times are the inverses of the corresponding exchange rates, $\Gamma_i=1/\tau_i$ which are mathematically equivalent parameters, but may be more useful.

Assuming subject 12 breathes at a constant rate, the portion of the lung's gas exchanged with the outside world in one breath, $F_{breath}$, may be shown in the following equation (3):

$$F_{breath}=1-f_1 e^{-t_b/\tau_1}-f_2 e^{-t_b/\tau_2} \quad (3)$$

wherein $t_b$ is the time of one breath. For illustrative purposes, parameter values which correspond to a normal adult subject at rest are assumed to be $t_b=4$ seconds; $\tau_1=40$ seconds; $f_1=1$; and $f_2=0$. This gives the following equation (4):

$$F_{breath}=9.52\%. \quad (4)$$

If, instead, 20% of the lung is almost completely blocked and the parameters are assumed to be $t_b=4$ seconds, $\tau_1=40$, $\tau_2=400$ seconds, $f_1=0.80$, and $f_2=0.20$, then as shown in the following equation (5):

$$F_{breath}=7.81\% \quad (5)$$

which is 82% of normal.

Figure 6:
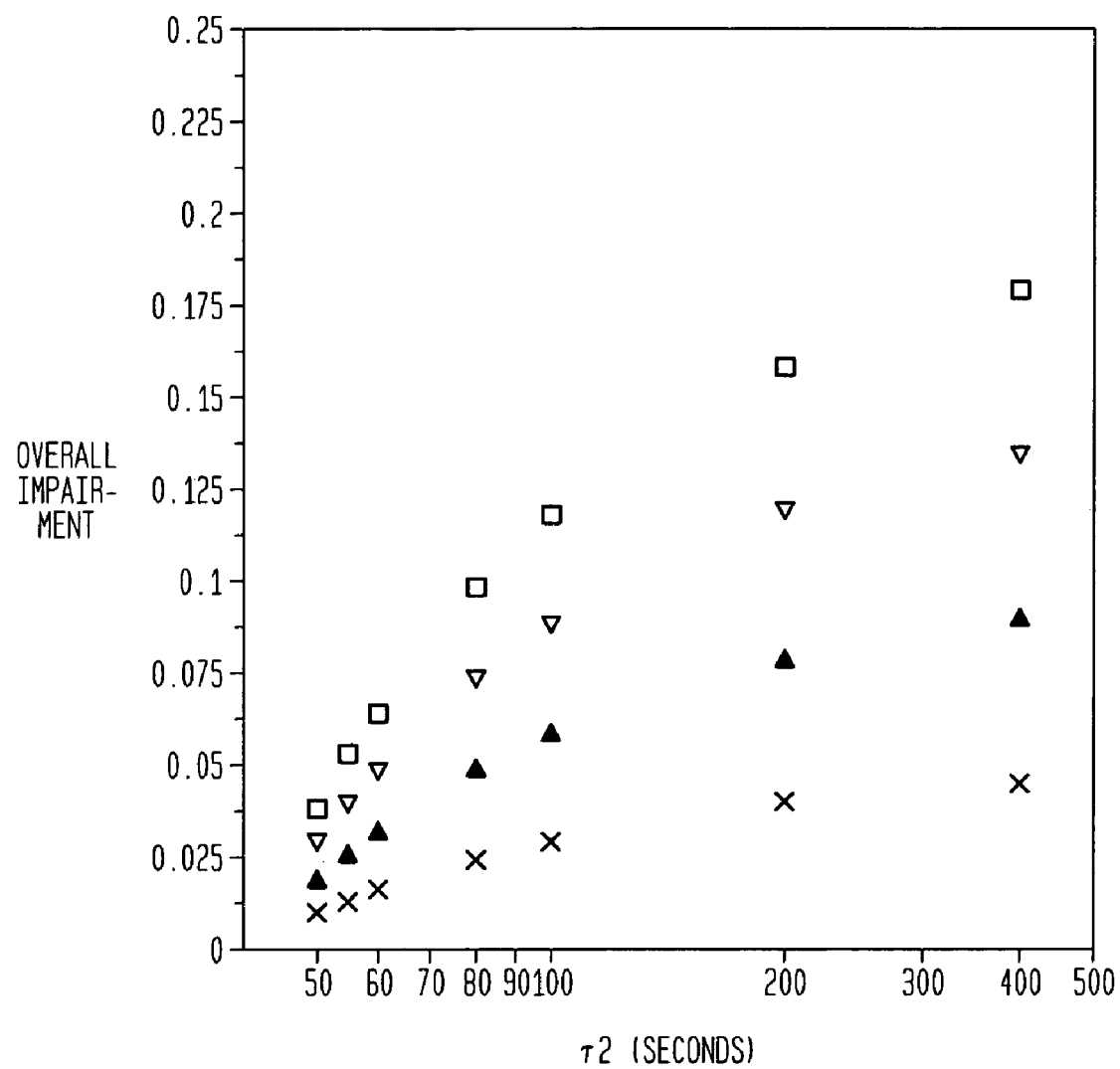
FIG. 6 is a graphical representation of a new measure of pulmonary impairment, the overall impairment, I, as a function of $\tau_2$ for $f_2=5\%$ (indicated by x's), 10% (indicated by triangles pointing up), 15% (indicated by triangles pointing down), and 20% (indicated by squares), all for $\tau_1=40$ seconds and $t_b=4$ seconds.

A new measure of pulmonary impairment, the overall impairment, I, may be defined to be the fractional reduction of $F_{breath}$ determined with two components (i.e., two mathematical fractions $f_1$ and $f_2$), which may be compared to that with only the first (one) component in the following equation (6):

$$I = 1 - \frac{F_{breath}^{two\ components}}{F_{breath}^{one\ component}} \quad (6)$$

wherein $F_{breath}^{one\ component}$ is $F_{breath}=1-f_1 e^{-t_b/\tau_1}$, $F_{breath}^{two\ components}$ is $F_{breath}=1-f_1 e^{-t_b/\tau_1}-f_2 e^{-t_b/\tau_2}$, $f_2$ is >0, and $\tau_1$ and $\tau_2$ have different values. In the example above, I=18%. FIG. 6 shows the values of impairment which correspond to various combinations of $f_2$ and $\tau_2$ for $\tau_1=40$ seconds and $t_b=4$ seconds. For any value of $f_2$, the overall impairment defined in this way depends only upon the ratios of $\tau_2$ to $\tau_1$ and $t_b$ so that these results, and those discussed below, may be easily generalized by one skilled in the art to, for example, account for the differences in $t_b$ from one subject to another, or for one subject from one set of measurements to another set of measurements. Similarly, the overall impairment, I, may be easily generalized by one skilled in the art to a model in which the predicted value of $f(t)$ in the $i^{th}$ breath may be written, for example as the following equation (7):

$$f(t_i)^{pred}=f_1 e^{-t_i/\tau_1}+f_2 e^{-t_i/\tau_2}+f_3 e^{-t_i/\tau_3} \quad (7).$$

Ideally, a measuring system should be more sensitive to lower levels of impairment than are current FEV1 tests, and should be sufficiently precise to allow small changes to be monitored quantitatively. Various embodiments of system 10 of the present invention may be able to do this by measuring $f_1$, $f_2$, $\tau_1$, and $\tau_2$ (under a variety of conditions) to provide additional information about the extent and level of small airway restriction. This additional information may include: (a) the ratio $f_2/f_1$ which specifically quantifies the portion of the lung which is effectively impaired and (b) the ratio $\tau_2/\tau_1$ which quantifies the level of impairment in the effectively impaired portion of the lung. By measuring these parameters, it is also possible to: (c) calculate the overall impairment, I, as defined by equation (6) above, which summarizes the results in a single number. If the parameters $f_1$, $f_2$, $\tau_1$, and $\tau_2$ are measured for a subject at rest, and then for the same subject exercising, the variations in the results may provide information related to the additional lung volumes recruited during exercise. Similarly, comparing the parameters measured with the subject sitting (or standing), with the parameters measured with the same subject lying down, may provide information about ventilation inhomogeneities in different physical portions of the lung as these different physical portions of the lung participate in ventilation differentially depending upon the position of the subject.

The sensitivity of system 10 may be quantified both in terms of how well $f_2$ and $\tau_2$ may be determined for standard values of $\tau_1$ and $t_b$, and in terms of how well the overall impairment, I, may be determined. How well the values $f_1$, $f_2$, $\tau_1$, $\tau_2$ and I are determined may depend upon how well the inert gas concentration can be measured by system 10 as a function of that inert gas concentration and upon the absolute range of inert gas concentrations which can be measured. As $f_2$ increases, system 10 may be able to measure values of $\tau_2$ closer to $\tau_1$, and as $\tau_2$ diverges from $\tau_1$, system 10 may be able to measure smaller values of $f_2$.

A measurement according to an embodiment of the method and system of the present invention may be simulated using Monte Carlo methods. This simulation assumes inert gas concentration measurements are measured with the sensitivities described in detail below, and which may be realized using either existing inert gas measurement technologies or extensions to such technologies. For each "experiment", the true inert gas concentration as a function of time may be generated as the sum of two exponential terms which total 80% at t=0. "Measurements" may be taken every four seconds, and the measured values fluctuate around the true values according to gas concentration sensitivity functions corresponding to the model embodiment. For each experiment, the measurements may be fitted to the sum of two exponential terms (see equation (1) above with $f_2$, $f_2$, $\tau_1$, and $\tau_2$ as free variables), minimizing $\chi^2$ over the range of measurements where the inert gas concentration measuring device 128 has sufficient sensitivity. Ensembles of experiments with the same true parameters may be generated, and statistical analyses of the measured parameters may enable characterizations of how well these parameters are measured.

Figure 7:
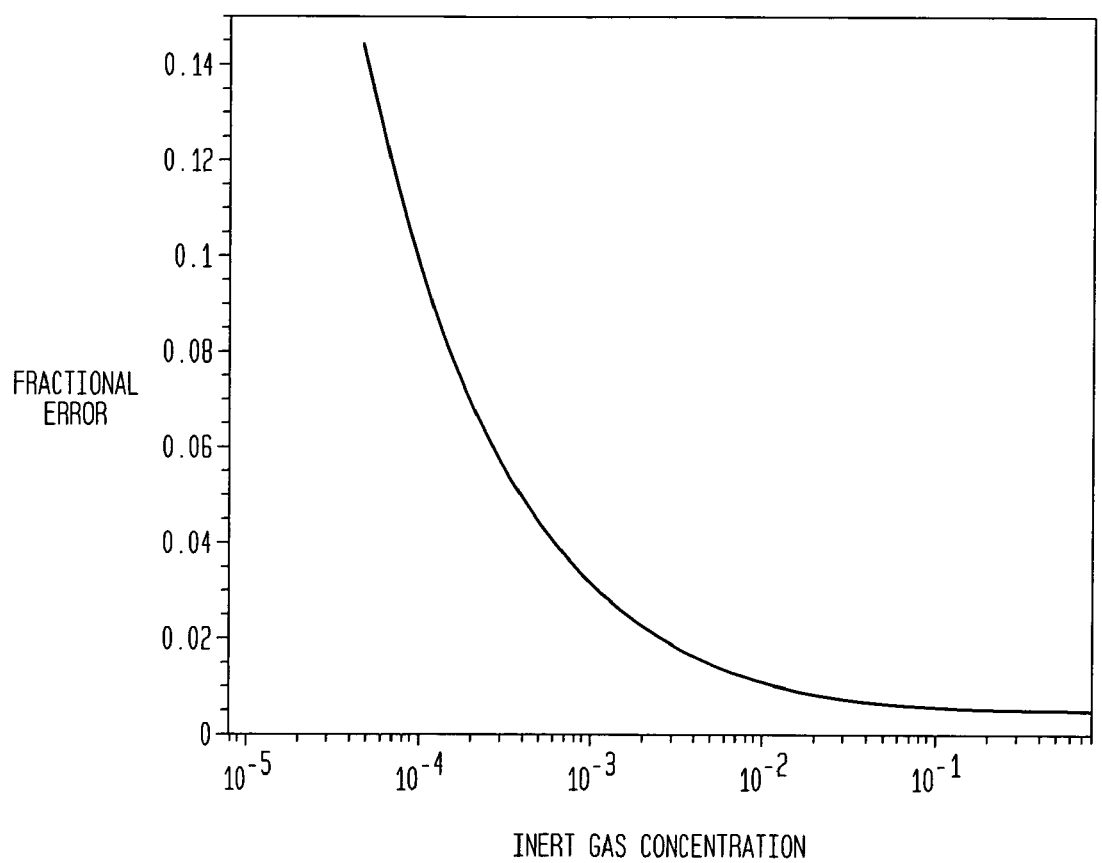
FIG. 7 is a graphical representation of a gas concentration sensitivity model used for Monte Carlo computer simulations of the characteristics of the system of FIGS. 1-4 with the vertical scale showing the fractional precision with which the inert gas concentration is assumed to be measured.

FIG. 7 graphically shows the fractional error as a function of the inert gas concentration in a Monte Carlo simulation of a model embodiment. The following equation (8) may be used to generate the curve in the plot shown in FIG. 7:

$$\frac{\Delta C}{C} = \sqrt{\left(\frac{0.001}{\sqrt{C}}\right)^2 + 0.005^2} \quad (8)$$

wherein C is the concentration and $\Delta C$ is the absolute uncertainty of concentration C. The term proportional to $1/\sqrt{C}$ accounts for statistical fluctuations in signal levels expected at low inert gas concentrations. For example, if the signal is detected using atomic emissions spectroscopy, $\Delta C$ may account for the statistical fluctuations in the number of detected photons. If the signal is detected using a mass spectrometer, $\Delta C$ may account for the statistical fluctuations in the number of ions detected. The numerator of the ratio on the right side of equation (7), namely 0.001, produces≈10% fractional error at a concentration of $10^{-4}$, and this ratio may be added in quadrature to 0.5% which appears to be a conservative estimate of the systematic uncertainties associated with a number of technologies. If making more precise measurements of $f_2$ and $\tau_2$ is important, one skilled in the art may reexamine the issue of the concentration range and precision required using the techniques described herein.

Figure 8:
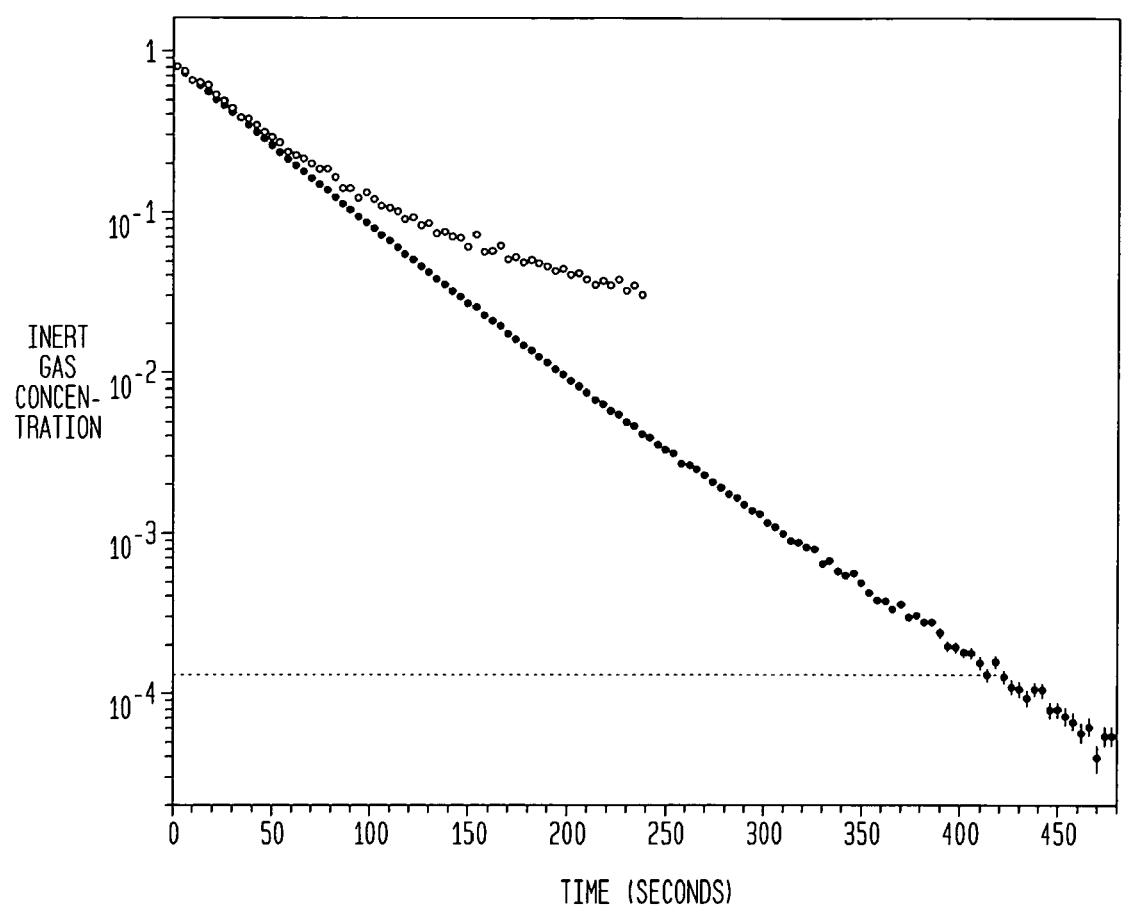
FIG. 8 is a graphical representation depicting the results of Monte Carlo computer simulations related to inert gas concentration measurements by the system of FIGS. 1-4, compared to inert gas concentration measurements using prior technology (FIG. 5), where the longer, lower, more linear set of points obtained from measurements by the system of FIGS. 1-4 is a typical Monte Carlo experiment generated with an initial inert gas concentration of 80%, of which 68% has $\tau_1=40$ seconds and 12% has $\tau_2=60$ seconds, and compared with the simulation of FIG. 5 which is shown as the upper set of points defining a shorter, more curved line.

FIG. 8 graphically shows the results of a typical Monte Carlo experiment using an embodiment of the method and system of the present invention (e.g., as illustrated in FIGS. 1-4) for $f_1$=0.68, $f_2$=0.12, $\tau_1$=40 seconds, and $\tau_2$=60 seconds. At 420 seconds the inert gas concentration has dropped from 0.80 to $1.3\times10^{-4}$. From a collection of many experiments generated with these parameters, it is found that $<f_2>$=0.123 with standard deviation of 0.015 and $<\tau_2>$=59.8 seconds with standard deviation 1.1 seconds. The average overall impairment is found to be $<I>$=3.3% with standard deviation 0.5%. The biases in the measured values of $<f_2>$ and $<\tau_2>$ are statistically real, but small compared to their standard deviations, and are thus not significant. Also shown in FIG. 8 is the simulation of FIG. 5 relating to a nitrogen washout measurement with parameters corresponding to those extracted from measurement shown in Levitzky, supra, referred to previously. From FIG. 8, the greater dynamic range of an embodiment of the method and system of the present invention is evident. As shown by FIG. 8, a system which has only two orders of magnitude sensitivity may not detect the non-exponential character that is simulated. For a similar collection of experiments with $\tau_2$ reduced to 55 seconds, it is found that $<I>$=2.9% with standard deviation 0.8% when measurements are made over 400 seconds, at which time the inert gas concentration has dropped to $0.9\times10^{-4}$. As I increases (decreases), it may be measured with better (worse) precision. Thus, these results indicate the approximate limit of sensitivity for I, given the inert gas concentration precision in this model. If greater sensitivity for I is needed to make specific pulmonary function measurements, one skilled in the art may determine the requisite inert gas concentration measurement precision.

While the precise model of gas exchange used above is an approximation to a much more complex reality, it may accurately illustrate the ability of system 10 to discriminate quantitatively between normal pulmonary function and pathological pulmonary function which reduces gas exchange in a portion of the lung. Similarly, while the mathematics used assumes that subject 12 breathes at a constant rate, this assumption may be relaxed with only a small increase in complexity using techniques well known to one skilled in the art.

Similarly, gas exchange between the lungs and the circulatory system may be quantified using the inert gas MBW method described above wherein the function f(t) has at least one exponential parameter having a characteristic inert gas concentration decay rate and having a coefficient which does not vary with time, which represents the circulatory system as an extension of the lung of the subject.

In one embodiment, inert gas composition 31 may contain only one physiologically acceptable inert gas. In another embodiment, inert gas composition 31 may contain two or more inert gases to allow a comparison of the parameters associated with the decay of each component's concentration. This comparison may provide either redundancy or complementarity depending upon the gases used. If the diffusion constants of the gases are very different, the differences in the extracted parameters may relate to the nature of the small airway restrictions. If the diffusion constants of the inert gases are similar, a mixture may be matched to the sensitivities of the inert gas concentration measuring device 128 to provide a greater dynamic range.

In one embodiment, inert gas composition 31 may comprise two or more inert gases, and wherein the concentration of the inert gas composition is measured by the inert gas concentration measuring device 128 over different, but overlapping, effective dynamic ranges, to thereby provide a greater overall effective dynamic range.

In one embodiment, the inert gas concentration measuring device 128 may be specialized to a single species of inert gas concentration. In another embodiment, the inert gas concentration measuring device 128 may measure a variety of inert gas concentrations.

In one embodiment, the inert gas concentration measuring device 128 may measure the inert gas concentration absolutely. In another embodiment, the inert gas concentration measuring device 128 may measure the ratio of the inert gas concentration relative to that of one or more other components of the exhaled breath which is/are monitored concurrently using another device. For example, the inert gas concentration may be measured relative to the oxygen, carbon dioxide and/or water level in the exhaled breath, the absolute concentrations of which may be measured with greater precision using commercially available technologies.

In one embodiment, the inert gas composition 31 and the replacement gas composition 33 may contain equal concentrations of an extra inert gas. Thus, the concentration of the extra inert gas in both inspired and exhaled breath does not vary as a function of time, and its concentration in the exhaled breath may therefore serve as a constant reference for relative inert gas concentration measurements, as described above.

In one embodiment, system 10 may incorporate a flow meter (not shown) to continuously monitor the rate at which a gas composition is inspired by subject 12. In another embodiment, system 10 may incorporate a flow meter 124 to continuously monitor the rate at which a gas composition is exhaled by subject 12 and/or to measure how much gas composition is exhaled in each breath by subject 12.

In one embodiment, system 10 may incorporate a means for determining the rate of respiration by subject 12.

In one embodiment, the inert gas concentration measuring device 128 may measure the ratio of inert gas concentrations to other gases present in exhaled breath.

In one embodiment, the inert gas concentration measuring device 128 may comprise a mass spectrometer to measure the absolute or relative gas concentrations of interest. In another embodiment, the inert gas concentration measuring device 128 may use the absorption of infrared light at wavelengths characteristic of the physiologically acceptable inert gas, and possibly of other gases (e.g., oxygen, carbon dioxide, etc.) present in exhaled breath, or the difference between thermal conductivities of the gases, to measure the absolute or relative gas concentrations of interest. In another embodiment, the inert gas concentration measuring device 128 may use an infrared light, visible light, or ultraviolet light spectrometer in conjunction with a laser stimulation, RF production of a gas plasma or cold cathode production of a gas plasma, to measure the absolute or relative gas concentrations of interest.

In another embodiment, the inert gas concentration measuring device 128 may use differences in speeds of ultrasonic waves to measure at least one inert gas concentration. In another embodiment, the inert gas concentration measuring device 128 may use measurements of the radioactive decay products of radioactive isotopes to measure at least one inert gas concentration. In another embodiment, the inert gas concentration measuring device 128 may use photoacoustic spectroscopy to measure at least one inert gas concentration. In other words, the inert gas concentration measuring device 128 may use existing, "off-the shelf" technologies providing sufficient sensitivity at an acceptable cost.

In one embodiment, the inert gas concentration in the inert gas composition 31 may be as high as is safe to breathe (approximately 80%) to provide the greatest dynamical range when using an inert gas concentration measuring device 128 with limited sensitivity. In another embodiment, the inert gas concentration in the inert gas composition 31 may be less than 80% to reduce the cost of the inert gas consumed during measurements.

In one embodiment, the controller 22 may have real-time firmware or software to analyze the inert gas concentration data (i.e., extract parameters), and to use the information or data extracted from this analysis to control the inert gas concentration measuring device 128. For example, if the detector used by the inert gas concentration measuring device 128 is a mass spectrometer, the firmware or software may control the length of time for accumulating data at any charge-to-mass ratio to optimize the overall sensitivity of the measurements. Similarly, if the inert gas concentration measuring device 128 is an atomic emissions spectrometer 300, the firmware or software may be used to control the integration time to avoid saturation at high concentrations and assure sufficient sensitivity at low concentrations.

In one embodiment, the data acquisition system may record the signals produced by the inert gas detector used with the inert gas concentration measuring device 128, and the times at which the signals are produced. In one embodiment, the data acquisition system may record signals from other detectors, including, but not limited to, pressure sensors, gas flow meters, oxygen meters, carbon dioxide meters, blood oxygen content meters, pulse monitors, nitric oxide monitors, etc. Acquiring data with these other devices concurrently may enable a clinician, investigator, etc., to associate information or data obtained, derived, etc., from system 10 with other information or data provided by other detectors to draw conclusions with respect to a subject's pulmonary condition which may not be possible using only information/data from system 10 or the other detectors.

In one embodiment, the controller 22 may have software to provide real-time analysis of the data collected, to record the data collected in a form that may be transmitted to an external device, and/or to transmit the data colleted to another device for recording. In another embodiment, the controller 22 may lack real-time analysis software, but may record the data in a form that may be transferred to an external device, may transmit the data to another device for data analysis, or both record and transmit the data to another device for analysis.

In one embodiment, the protocol for measuring lung function may involve one or more cycles in which subject 12 breathes various inert gas compositions (e.g., gas mixtures) for periods of time followed by periods of time during which the subject breathes replacement gas composition 33 while the inert gas concentration(s) is(are) measured. For example, the protocol may include a period during which subject 12 breathes ordinary air followed by a period during which the subject breathes, for example, an argon/oxygen mixture with the nitrogen portion being measured, followed by a period during which the subject breathes a nitrogen/oxygen mixture with the argon portion being measured. Making multiple measurements with the same inert gas composition may enable a systematic check that the measurement is correct or accurate. Conversely, making multiple measurements with different inert gas compositions may enable similar or complementary systematic checks.

In one embodiment, a second protocol for measuring lung function may involve one or more measurement cycles in which subject 12 is exercising at an elevated rate of respiration while breathing the replacement gas composition 33. This may increase the sensitivity to small airway restriction as a larger portion of the air exchanged in each breath originates in small airways rather than in anatomic dead space.

In one embodiment, the non-exponential character of $f(t)$ may be extracted as a sum of two (or more) exponential terms using a $\chi^2$ minimization fit or maximum likelihood fit. In another embodiment, the non-exponential character of $f(t)$ may be extracted by comparison to template forms based on models or observations or by using neural networks trained on measurements made using a variety of populations including healthy individuals and diseased individuals with known pathologies. Using template forms or neural networks based on empirical observation of healthy and diseased subjects may eliminate some model dependencies in interpreting the results.

In one embodiment, the function $f(t)$ has at least one exponential term having a characteristic inert gas concentration decay rate and having a coefficient which does not vary with time, which represents the circulatory system as an extension of the lung of the subject. This may enable the clinician or researcher to mathematically characterize the circulatory system of the subject quantitatively and may discriminate between healthy subjects and those with pathologies related to restricted blood flow in parts of the body.

In one embodiment, a digital summary of results and/or raw measurements may be stored digitally as part of a subject's record. This may enable a comparison of a subject's pulmonary function states at different times, as well as a comparison of this subject's pulmonary function state with that of other subjects. In another embodiment, raw data and summaries of measurements for many subjects may be stored digitally, while protecting the privacy of the subjects, so that the information is available to researchers for future analysis.

In one embodiment, software may be used to extract parameters describing the non-exponential character of the inert gas washout fraction accounting for the variability of integrated gas flow in each breath by including a suitable breath-by-breath correction to account for the duration of each breath and its integrated flow rate or by including a suitable systematic uncertainty to account for variations in the duration of each breath and its integrated flow rate.

In one embodiment, the gas supply system may comprise single cylinders of premixed gas compositions, each of which feeds a single instance of system 10 (i.e., one subject interface 122, inert gas concentration measuring device 128, one controller 22, etc.). In another embodiment, the gas supply system may comprise a bank of cylinders or other containers of premixed gas compositions, each of which feeds a single instance, or multiple instances, of the system. In another embodiment, a gas-mixing station may create the inert gas composition 31 and/or the replacement gas composition 33 with the specific concentration(s) desired.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A Method comprising the following steps:
   (1) providing a measurement of a subject breathing an inert gas composition;
   (2) providing a measurement of the subject breathing a replacement gas composition; and
   (3) identifying and quantifying any presence of a partially blocked or constricted small airway in a lung of the subject based on an inert gas concentration function; $f(t)$, defined by extracting parameters with a controller or a computer processor from the inert gas composition measurement and the replacement gas composition measurement, wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time.

2. The method of claim 1, wherein step (3) is carried out to measure overall impairment, I, of pulmonary function of the subject according to the following equation:

$$I = 1 - \frac{F_{breath}^{two\ components}}{F_{breath}^{one\ component}}$$

wherein $F_{breath}^{one\ component}$ is $F_{breath}=1-f_1 e^{-t_b/\tau_1}$, $F_{breath}^{two\ components}$ is $F_{breath}=1-f_1 e^{-t_b/\tau_1}-f_2 e^{-t_b/\tau_2}$, $f_2$ is $>0$, and $\tau_1$ and $\tau_2$ have different values.

3. The method of claim 1, wherein the inert gas composition of step (1) comprises nitrogen, helium, neon, argon, krypton, xenon, radon, sulfur hexafluoride, a perfluorocarbon or a mixture thereof.

4. The method of claim 1, wherein function $f(t)$ of step (3) is the sum of two exponential terms having characteristic inert gas concentration decay rates $\Gamma_1$ and $\Gamma_2$ and corresponding coefficients $f_1$ and $f_2$.

5. The method of claim 4, wherein step (3) is carried out to measure a portion of a lung's gas exchanged with the outside world in one breath, $F_{breath}$, according to the following equation:

$$F_{breath}=1-f_1 e^{-t_b/\tau_1}-f_2 e^{-t_b/\tau_2}$$

wherein $\tau_1$ is the characteristic decay time of fraction $f_1$, wherein $\tau_2$ is the characteristic decay time of fraction $f_2$, and $t_b$ is the time period for a single breath.

6. A method comprising the following steps:
   (1) providing a measurement of a subject breathing an inert gas composition;
   (2) providing a measurement of the subject breathing a replacement gas composition; and
   (3) quantifying the inert gas washout from the circulatory system of the subject based on an inert gas concentration function, $f(t)$, defined by extracting parameters with a controller or a computer processor from the inert gas composition measurement and the replacement gas composition measurement, wherein the circulatory system of the subject is treated as an extension of the lung of the subject, and wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time.

7. The method of claim 6, wherein the function $f(t)$ of step (3) is the sum of two exponential terms having characteristic inert gas concentration decay rates $\Gamma_1$ and $\Gamma_2$ and corresponding coefficients $f_1$ and $f_2$.

8. A system comprising: (a) a gas supply; (b) a subject interface; (c) an inert gas concentration measuring device; and (d) means for extracting parameters from the measurements by the inert gas concentration measuring device; wherein the system:
   (1) obtains a measurement with the inert gas concentration measuring device through the subject interface of a subject breathing an inert gas composition supplied from the gas supply;
   (2) obtains a measurement with the inert gas concentration measuring device through the subject interface of the subject breathing a replacement gas composition from the gas supply; and
   (3) extracts parameters with the parameter extracting means from the inert gas composition measurement and the replacement gas composition measurement that define an inert gas concentration function, $f(t)$, to thereby: (a) define an extent and level of small airway restriction in a lung of the subject; or (b) quantify an inert gas washout from the circulatory system of the subject, wherein the function $f(t)$ is the sum of at least two exponential terms defining different effective volumes of the lung of the subject, each exponential term having a characteristic inert gas concentration decay rate, $\Gamma_i$, and a corresponding coefficient, $f_i$, which does not vary with time.

9. The system of claim 8, wherein the inert gas concentration measuring device uses mass spectroscopy to measure inert gas concentration.

10. The system of claim 8, wherein the inert gas concentration measuring device uses infrared absorption to measure inert gas concentration.

11. The system of claim 8, wherein the inert gas concentration measuring device uses atomic emissions spectroscopy to measure inert gas concentration.

12. The system of claim 11, wherein the inert gas concentration measuring device uses laser stimulation in conjunction with atomic emissions spectroscopy to measure inert gas concentration.

13. The system of claim 8, wherein the inert gas concentration measuring device uses differences in thermal conductivity to measure inert gas concentration.

14. The system of claim 8, wherein the inert gas concentration measuring device uses differences in speeds of ultrasonic waves to measure inert gas concentration.

15. The system of claim 8, wherein the inert gas concentration measuring device uses measurements of the radioactive decay products of radioactive isotopes to measure inert gas concentration.

16. The system of claim 8, wherein the inert gas concentration measuring device uses photoacoustic spectroscopy to measure inert gas concentration.

17. The system of claim 8, wherein the parameter extracting means comprises a computer.

18. The system of claim 17, wherein the computer also functions as a controller to adjust operating conditions of the inert gas concentration measuring device during operation of the system to optimize sensitivity.

19. The system of claim 8, wherein the inert gas concentration measuring device measures an inert gas component in an exhaled breath of the subject relative to another component in the exhaled breath.

20. The system of claim 19, wherein the another component comprises one or more of oxygen, carbon dioxide or water.

21. The system of claim 8, wherein the inert gas composition and the replacement gas composition each contain equal fractions of a physiologically acceptable inert gas as a reference.

22. The system of claim 8, wherein the inert gas composition comprises at least two inert gases, and wherein the concentration of the inert gas composition is measured by the inert gas concentration measuring device over different, but overlapping, effective dynamic ranges, to thereby provide a greater overall effective dynamic range.

23. The system of claim 8, wherein the system defines the extent and level of small airway restriction in a lung of the subject.

24. The system of claim 8, wherein the system quantifies the inert gas washout from the circulatory system of the subject.

\* \* \* \* \*

UNITED STATES PATENT AND TRADEMARK OFFICE
CERTIFICATE OF CORRECTION

| | | |
|---|---|---|
| PATENT NO. | : 7,993,278 B2 | |
| APPLICATION NO. | : 11/485394 | |
| DATED | : August 9, 2011 | |
| INVENTOR(S) | : Michael Sokoloff | |

It is certified that error appears in the above-identified patent and that said Letters Patent is hereby corrected as shown below:

At column 2, lines 6, 8, 37, 40, 59, and 61, each instance of "$f$(t)" should be -- $f(t)$ --.

At column 2, lines 11, 44, and 64, each instance of "Γ$_i$" should be -- $\Gamma_i$ --.

At column 2, lines 14 and 22, each instance of ", I," should be -- , $I$, --.

At column 2, lines 17 and 49, each instance of "F$_{breath}$" should be -- $F_{breath}$ --.

At column 2, line 48, "t$_b$" should be -- $t_b$ --.

At column 3, line 2, "t$_b$" should be -- $t_b$ --.

At column 3, lines 19 and 23, each instance of "$f$(t)" should be -- $f(t)$ --.

At column 3, line 26, "Γ$_i$" should be -- $\Gamma_i$ --.

At column 3, line 56, ", I," should be -- , $I$, --.

At column 4, line 65, "$f$(t)" should be -- $f(t)$ --.

At column 5, line 6, "$Ce^{-\Gamma t}$" should be -- $Ce^{-\Gamma t}$ --, after "where," "C" should be -- $C$ -- and "t" after "symbol" should be -- $t$ --.

At column 5, line 13, "Γ$_i$" should be -- $\Gamma_i$ --.

At column 5, line 23, "Γ$_1$" should be -- $\Gamma_1$ --, and "Γ$_2$" should be -- $\Gamma_2$ --.

At column 5, line 25, "Γ$_3$" should be -- $\Gamma_3$ --, and "Γ$_4$" should be -- $\Gamma_4$ --.

Signed and Sealed this
Twenty-seventh Day of March, 2012

David J. Kappos
*Director of the United States Patent and Trademark Office*

CERTIFICATE OF CORRECTION (continued)
U.S. Pat. No. 7,993,278 B2

At column 5, line 30, "$\Gamma$" should be -- $\varGamma$ --, "$\Gamma_1$" should be -- $\varGamma_1$ --, and "$\Gamma_2$" should be -- $\varGamma_2$ --.

At column 5, line 43, "$\Gamma$" should be -- $\varGamma$ --, "$\Gamma_1$" should be -- $\varGamma_1$ --, and "$\Gamma_2$" should be -- $\varGamma_2$ --.

At column 5, line 54, "$\Gamma_1$" should be -- $\varGamma_1$ --.

At column 5, line 55, "$\Gamma_2$" should be -- $\varGamma_2$ --, and "$\Gamma_1$" should be -- $\varGamma_1$ --.

At column 5, line 57, "$\Gamma_2$" should be -- $\varGamma_2$ --.

At column 6, line 55, "C" after "quantity" should be -- $C$ --, "$\Delta C/C$" should be -- $\varDelta C/C$ --, and "$\Delta C$" should be -- $\varDelta C$ --.

At column 7, line 10, ""I"" after "characterized as" should be -- "$I$" --.

At column 7, line 19, "$t_b$" should be -- $t_b$ --.

At column 7, the equation at line 41 should appear as -- $\sqrt{x^2 + y^2}$ --.

At column 8, line 8, each instance of "$f$(t)" should be -- $f(t)$ --.

At column 8, line 34, "$\Gamma_1$" should be -- $\varGamma_1$ --.

At column 8, line 34, "$\Gamma_2$" should be -- $\varGamma_2$ --.

At column 10, line 22, "$f$(t)" should be -- $f(t)$ --.

At column 10, line 46, "$f$(t)" should be -- $f(t)$ --, and "$f(t_i)^{pred}$" should be -- $f(t_i)^{pred}$ --.

At column 10, line 50, "$t_i$" should be -- $t_i$ --.

At column 11, line 50, ", I," should be -- , $I$, --.

At column 11, line 51, "$F_{breath}$" should be -- $F_{breath}$ --.

At column 11, lines 61-62 should read as follows:

wherein $F_{breath}^{one\ component}$ is $F_{breath} = 1 - f_1 e^{-t_b/\tau_1}$, $F_{breath}^{two\ components}$ is $F_{breath} = 1 - f_1 e^{-t_b/\tau_1} - f_2 e^{-t_b/\tau_2}$, $f_2$ is > 0, and $\tau_1$ and $\tau_2$ have different values. In the example above, --.

At column 11, line 66, "$t_b$" should be -- $t_b$ --.

CERTIFICATE OF CORRECTION (continued)
U.S. Pat. No. 7,993,278 B2

At column 12, line 7, "$f$(t)" should be -- $f(t)$ --.

At column 12, line 23, ", I," should be -- , $I$, --.

At column 12, line 40, after "and," "I" should read -- $I$ --.

At column 13, line 12, after "wherein," "C" should be -- $C$ --, and "ΔC" should be -- $\varDelta C$ --.

At column 13, line 13, after "concentration," "C" should be -- $C$ --, and the fraction at the end of line 13 should appear as -- $1/\sqrt{C}$ --.

At column 13, lines 16 and 19, each instance of "ΔC" should be -- $\varDelta C$ --.

In Claim 1, at column 17, line 22, "Method" should be -- method --.

In Claim 1, at column 17, lines 30 and 33, each instance of "$f$(t)" should be -- $f(t)$ --.

In Claim 1, at column 17, line 37, "Γᵢ" should be -- $\varGamma_i$ --.

In Claim 2, at column 17, line 40 ", I," should be -- , $I$, --.

In Claim 2, at column 17, lines 48-50 should appear as follows:

wherein $F_{breath}^{one\ component}$ is $F_{breath} = 1 - f_1 e^{-t_b/\tau_1}$, $F_{breath}^{two\ components}$ is $F_{breath} = 1 - f_1 e^{-t_b/\tau_1} - f_2 e^{-t_b/\tau_2}$, $f_2$ is $> 0$, and $\tau_1$ and $\tau_2$ have different values.

In Claim 4, at column 17, line 55, "$f$(t)" should be -- $f(t)$ --.

In Claim 5, at column 17, line 61, "F_breath" should be -- $F_{breath}$ --.

In Claim 5, at column 17, line 67, "t_b" should be -- $t_b$ --.

In Claim 6, at column 18, lines 8 and 13, each instance of "$f$(t)" should be -- $f(t)$ --.

In Claim 6, at column 18, line 17, "Γᵢ" should be -- $\varGamma_i$ --.

In Claim 7, at column 18, line 19, "$f$(t)" should be -- $f(t)$ --.

In Claim 7, at column 18, line 21, "Γ₁" should be -- $\varGamma_1$ --, and "Γ₂" should be -- $\varGamma_2$ --.

In Claim 8, at column 18, lines 39 and 43, each instance of "$f$(t)" should be -- $f(t)$ --.

In Claim 8, at column 18, line 46, "Γᵢ" should be -- $\varGamma_i$ --.